US009889307B2

(12) United States Patent
Meskens

(10) Patent No.: US 9,889,307 B2
(45) Date of Patent: Feb. 13, 2018

(54) INTERLEAVING POWER AND DATA IN A TRANSCUTANEOUS COMMUNICATIONS LINK

(75) Inventor: Werner Meskens, Opwijk (BE)

(73) Assignee: Cochlear Limited, Macquarie University, NSW (AU)

( * ) Notice: Subject to any disclaimer, the term of this patent is extended or adjusted under 35 U.S.C. 154(b) by 1445 days.

(21) Appl. No.: 12/391,029

(22) Filed: Feb. 23, 2009

(65) Prior Publication Data

US 2009/0216296 A1 Aug. 27, 2009

(30) Foreign Application Priority Data

Feb. 22, 2008 (AU) ................................ 2008900851

(51) Int. Cl.
*A61N 1/378* (2006.01)
*A61N 1/372* (2006.01)
*A61N 1/36* (2006.01)
*A61N 1/05* (2006.01)

(52) U.S. Cl.
CPC ....... *A61N 1/3787* (2013.01); *A61N 1/36032* (2013.01); *A61N 1/37252* (2013.01); *A61N 1/0541* (2013.01)

(58) Field of Classification Search
USPC .............................. 607/31, 32, 55–57, 60, 61
See application file for complete search history.

(56) References Cited

U.S. PATENT DOCUMENTS

| 5,814,089 | A * | 9/1998 | Stokes et al. ................... 607/32 |
| 6,249,704 | B1 * | 6/2001 | Maltan et al. .................. 607/57 |
| 6,275,737 | B1 * | 8/2001 | Mann .............................. 607/61 |
| 6,308,101 | B1 * | 10/2001 | Faltys et al. ..................... 607/57 |
| 6,334,072 | B1 | 12/2001 | Leysieffer |
| 6,533,733 | B1 | 3/2003 | Ericson et al. |
| 6,591,139 | B2 * | 7/2003 | Loftin et al. ................... 607/60 |
| 7,162,307 | B2 * | 1/2007 | Patrias .......................... 607/60 |
| 2004/0094355 | A1 | 5/2004 | Goorevich et al. |
| 2005/0004619 | A1 * | 1/2005 | Wahlstrand et al. .......... 607/45 |

(Continued)

FOREIGN PATENT DOCUMENTS

WO WO 2006/012371 2/2006
WO WO 2007/124325 11/2007

OTHER PUBLICATIONS

Extended European Search Report, European Application No. 09250467.9 dated Jun. 29, 2009 (9 pages).

(Continued)

*Primary Examiner* — William Levicky

(57) ABSTRACT

The present invention is related to an implantable medical device. The medical device comprises an implantable component having a receiver unit; an external charging module having a power transmitter unit; and a data module having a data transmitter unit. The units are configured to establish a transcutaneous communication link over which data and power is transmitted on a single frequency channel via a time interleaving scheme comprising successive frames each divided into at least two time slots, and wherein one or more of the time slots in each frame is allocated to the data transmitter unit, and wherein one or more of the time slots in each frame is allocated to the power transmitter unit, and wherein data and power are transmitted by the transmitter units during their allotted time slots.

31 Claims, 12 Drawing Sheets

(56) References Cited

U.S. PATENT DOCUMENTS

2006/0020304 A1    1/2006  Torgerson et al.
2006/0190059 A1*   8/2006  Griffith .......................... 607/57
2010/0305663 A1*  12/2010  Aghassian .................... 607/61

OTHER PUBLICATIONS

Hugh McDermott, "An Advanced Multiple Channel Cochlear Implant", IEEE Transactions on Biomedical Engineering, 36 Jul. 1989, No. 7, pp. 789-797 (9 pages).
Brian Smith et al., "An Externally Powered, Multichannel, Implantable Stimulator-Telemeter for Control of Paralyzed Muscle", IEEE Transactions on Biomedical Engineering, vol. 45, No. 4, Apr. 1998, pp. 463-475 (13 pages).

* cited by examiner

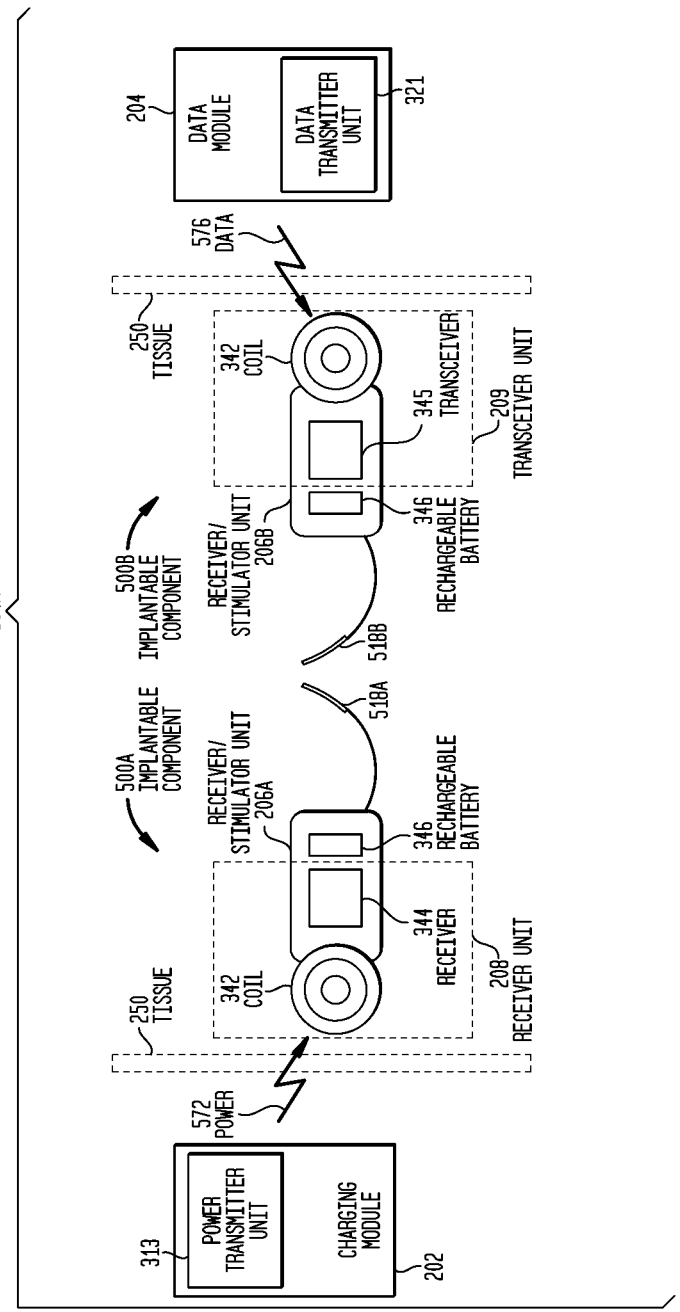

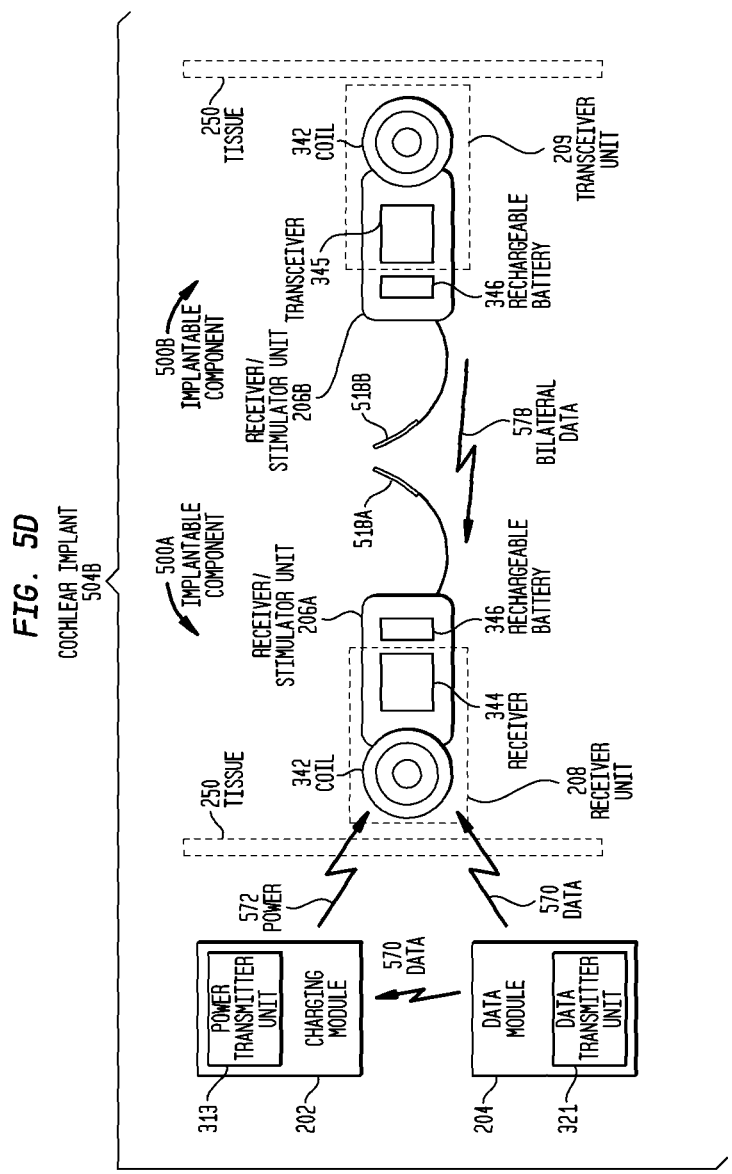

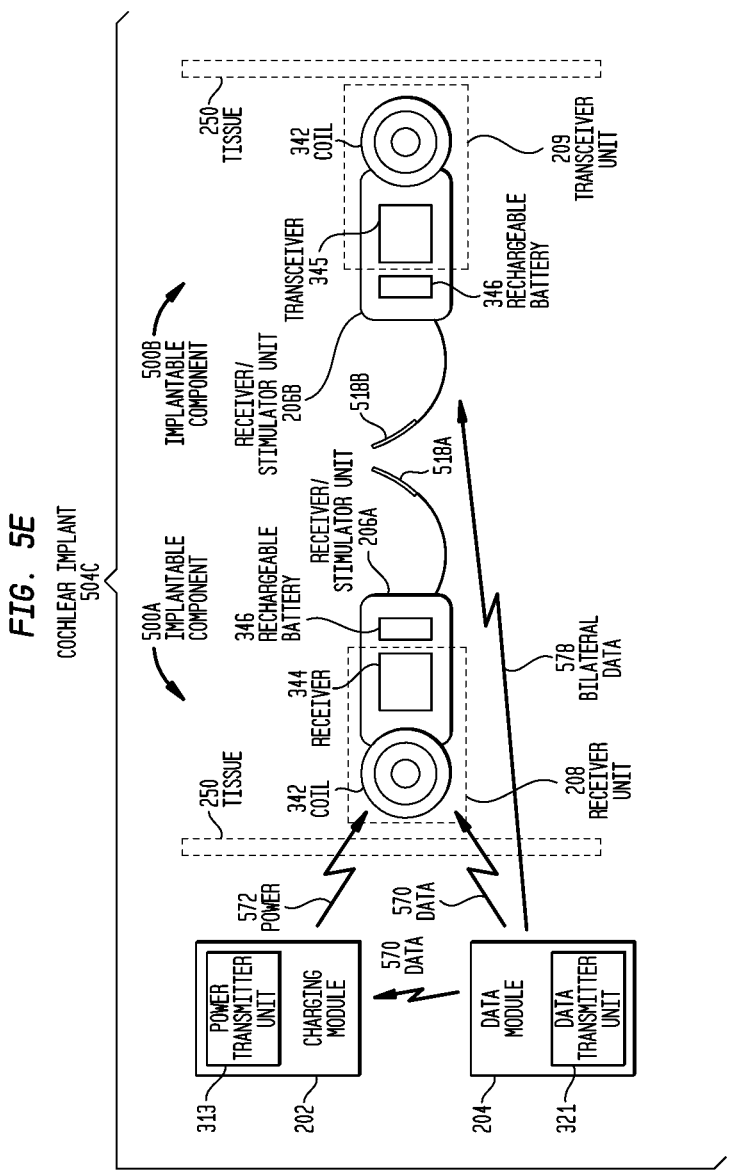

INTERLEAVING POWER AND DATA IN A TRANSCUTANEOUS COMMUNICATIONS LINK

CROSS-REFERENCE TO RELATED APPLICATIONS

The present invention claims the benefit of Australian Provisional Application No. 2008900851; filed Feb. 22, 2008. The content of this application is hereby incorporated by reference herein.

BACKGROUND

Field of the Invention

The present invention relates generally to transcutaneous communication in implantable medical devices and, more particularly, to interleaving power and data in a transcutaneous communication link.

Related Art

Medical devices having one or more implantable components, generally referred to as implantable medical devices, have provided a wide range of therapeutic benefits to patients over recent decades. In particular, devices such as hearing aids, implantable pacemakers, defibrillators, functional electrical stimulation devices, such as Cochlear™ prostheses, organ assist or replacement devices, and other partially or completely-implanted medical devices, have been successful in performing life saving and/or lifestyle enhancement functions for a number of years.

As such, the type of implantable devices and the range of functions performed thereby have increased over the years. For example, many such implantable medical devices often include one or more instruments, apparatus, sensors, processors, controllers or other functional mechanical, electrical or electronic components that are permanently or temporarily implanted in a patient to perform diagnosis, prevention, monitoring, treatment or management of a disease or injury or symptom thereof, or to investigate, replace or modify of the anatomy or of a physiological process. Many of these implantable components receive power and/or data from external components that are part of, or operate in conjunction with, the implantable component. In particular, many such implantable medical devices include a power source integrated into the implantable component. Some larger systems include more than one implantable component of which one is a power source which provides power to another implantable component. Such power sources are typically rechargeable batteries although other types of power sources have be implemented as well.

One such type of medical device is a Cochlear™ prosthesis (commonly referred to as a Cochlear™ prosthetic device, Cochlear™ implant, Cochlear™ device, and the like; simply "cochlear implants" herein.) Cochlear implants are to a specific type of hearing prostheses that deliver electrical stimulation to the cochlea of a recipient. As used herein, cochlear implants also include hearing prostheses that deliver electrical stimulation in combination with other types of stimulation, such as acoustic or mechanical stimulation.

SUMMARY

In accordance with one aspect of the present invention, a cochlear implant is provided. The cochlear implant comprises: an implantable component having an electrode assembly insertable in a recipient's cochlea and a stimulator/receiver unit configured to deliver stimulation signals to the recipient's cochlea via the electrode assembly; an external charging module having a power transmitter unit; and a data module having a data transmitter unit; wherein the units are configured to establish a transcutaneous communication link over which data and power is transmitted on a single frequency channel via a time interleaving scheme comprising successive frames each divided into at least two time slots, and wherein one or more of the time slots in each frame is allocated to the data transmitter unit, and wherein one or more of the time slots in each frame is allocated to the power transmitter unit, and wherein data and power are transmitted by the transmitter units during their allotted time slots.

In accordance with another aspect of the invention, a medical device is provided. The medical device comprises: an implantable component having a receiver unit; an external charging module having a power transmitter unit; and a data module having a data transmitter unit; wherein the units are configured to establish a transcutaneous communication link over which data and power is transmitted on a single frequency channel via a time interleaving scheme comprising successive frames each divided into at least two time slots, and wherein one or more of the time slots in each frame is allocated to the data transmitter unit, and wherein one or more of the time slots in each frame is allocated to the power transmitter unit, and wherein data and power are transmitted by the transmitter units during their allotted time slots.

BRIEF DESCRIPTION OF THE DRAWINGS

Embodiments of the present invention are described below with reference to the attached drawings, in which:

FIG. 5C is a schematic block diagram of a cochlear implant in accordance with one embodiment of the present invention;

FIG. 5D is a schematic block diagram of a cochlear implant in accordance with one embodiment of the present invention;

FIG. 5E is a schematic block diagram of a cochlear implant in accordance with one embodiment of the present invention.

DETAILED DESCRIPTION

Aspects of the present invention are generally directed to a transcutaneous communication link in an implantable medical device over which power and data are transmitted from independent sources to a single receiver unit within an implantable component. The power and data are time interleaved on a single frequency channel.

An implantable medical device in accordance with embodiments of the present invention comprises an implantable component having a receiver unit, an external power transmitter unit and a data transmitter unit. The units collectively establish the transcutaneous communication link. To transfer the power and data, the transcutaneous communication link implements a time interleaving scheme having successive time frames that are each divided into two or more time slots. One or more of the time slots in each frame is allocated to the data transmitter unit, and one or more of the time slots in each frame is allocated to the power transmitter unit. The data and power are transmitted by the respective transmitter units to the receiver unit during the time slots allocated thereto.

Although embodiments of the present invention are described herein primarily in connection with one type of implantable medical device, namely a Cochlear™ prosthesis (commonly referred to as a Cochlear™ prosthetic device, Cochlear™ implant, Cochlear™ device, and the like; simply "cochlear implants" herein), it would be appreciated that embodiments of the present invention may be implemented in any implantable medical device now known or later developed. Implantable medical devices envisaged by the present invention include, but are not limited to, cardiac monitors and defibrillators; glucose meters; implantable drug pumps; neural stimulators, including vision and hearing prostheses such auditory brain stimulators, or other devices that electrically, acoustically or mechanically stimulate components of the recipient's outer, middle or inner ear. It would also be understood that the present invention, though particularly applicable to implantable medical devices, may also be applied to a wide variety of other medical devices that do not include an implantable device.

Figure 1:
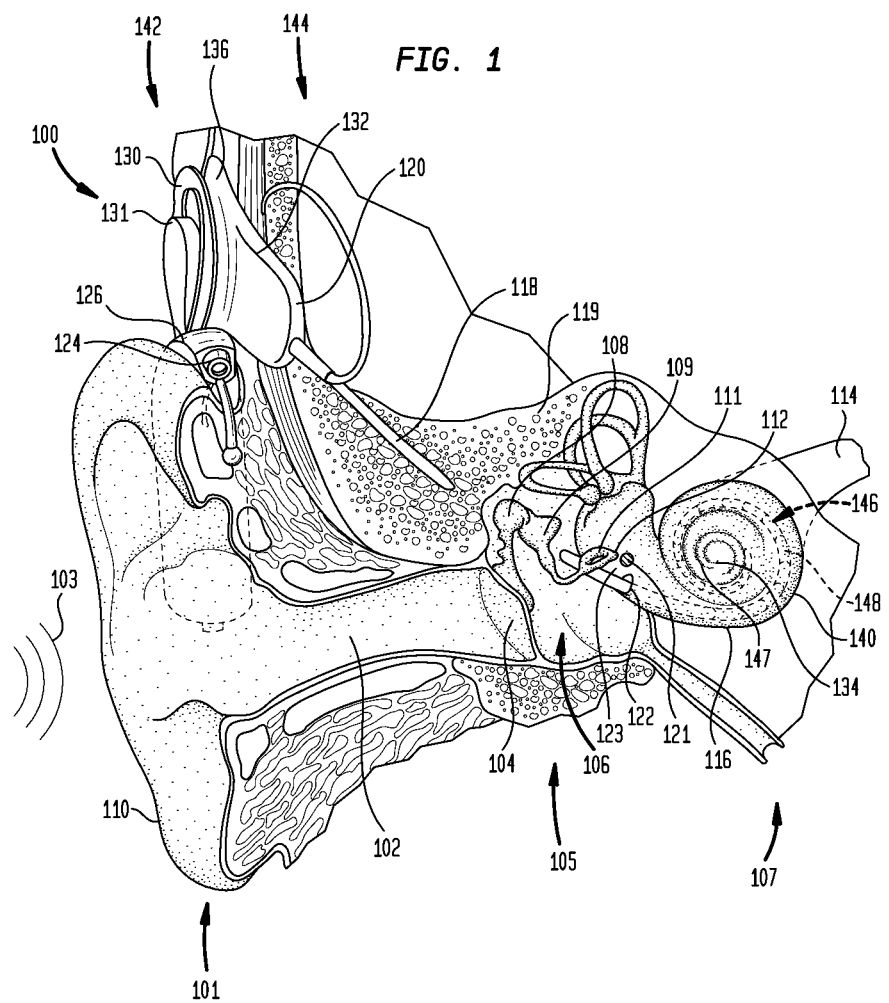
FIG. 1 is a perspective view of an exemplary medical device, namely a cochlear implant, in which embodiments of the present invention may be implemented.

FIG. 1 is perspective view of a cochlear implant, referred to as cochlear implant 100, implanted in a recipient. The recipient has an outer ear 101, a middle ear 105 and an inner ear 107. Components of outer ear 101, middle ear 105 and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channelled into and through ear canal 102. Disposed across the distal end of ear cannel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

As shown, cochlear implant 100 comprises an external component 142 which is directly or indirectly attached to the body of the recipient, and an internal or implantable component 144 which is temporarily or permanently implanted in the recipient. External component 142 may comprise one or more functional components which generate to receive data. For example, in the exemplary arrangement of FIG. 1, external component 142 comprises one or more sound input elements, shown as microphone 124 for detecting sound, and a sound processing unit 126. Sound processing unit 126 converts the sound received by microphone 124 into encoded data signals. As described in detail below, sound processing unit 126 may comprise a transmitter unit which transmits the encoded data signals to an internal receiver unit 132 in internal component 144. Also as described in greater detail below, in certain embodiments of the present invention, implantable component 144 may process the sound received by microphone 124. In such embodiments, the electrical signals output by microphone 124 are transmitted to implantable receiver unit 132.

External component 142 further comprises a charging module 131 configured to provide power to implantable component 144. As described in detail below, charging module 131 comprises a power source (not shown), a power transmitter (also not shown), an external coil 130, and, preferably, a magnet (also not shown) secured directly or indirectly to external coil 130. The power transmitter use external coil 130 to transmit power to internal component 144.

As noted, implantable component 144 comprises a receiver unit 132 which may be positioned in a recess of the temporal bone adjacent auricle 110 of the recipient. As detailed below, receiver unit 132 receives power and data via radio frequency (RF) links from external component 142. Receiver unit 132 comprises an internal coil 136, and preferably, a magnet (also not shown) fixed relative to the internal coil. Internal coil 136 is typically a wire antenna coil comprised of multiple turns of electrically insulated single-strand or multi-strand platinum or gold wire.

Implantable component 144 further comprises a stimulator unit 120 and an elongate electrode assembly 118. Internal receiver unit 132 and stimulator unit 120 are hermetically sealed within a biocompatible housing, sometimes collectively referred to as a stimulator/receiver unit 120. Elongate electrode assembly 118 has a proximal end connected to stimulator unit 120, and a distal end implanted in cochlea 140. Electrode assembly 118 extends from stimulator unit 120 to cochlea 140 through mastoid bone 119. Electrode assembly 118 is inserted or implanted into cochlea 104. In some embodiments electrode assembly 118 may be implanted at least in basal region 116, and sometimes further. For example, electrode assembly 118 may extend towards apical end of cochlea 140, referred to as cochlea apex 134. In certain circumstances, electrode assembly 118 may be inserted into cochlea 140 via a cochleostomy 122. In other circumstances, a cochleostomy may be formed through round window 121, oval window 112, the promontory 123 or through an apical turn 147 of cochlea 140.

Electrode assembly 118 comprises a longitudinally aligned and distally extending array 146 of electrodes 148, sometimes referred to as electrode array 146 herein, disposed along a length thereof. Although electrode array 146 may be disposed on electrode assembly 118, in most practical applications, electrode array 146 is integrated into electrode assembly 118. As such, electrode array 146 is referred to herein as being disposed in electrode assembly 118. Stimulator unit 120 generates stimulation signals which are applied by electrodes 148 to cochlea 140, thereby stimulating auditory nerve 114.

Figure 2A:
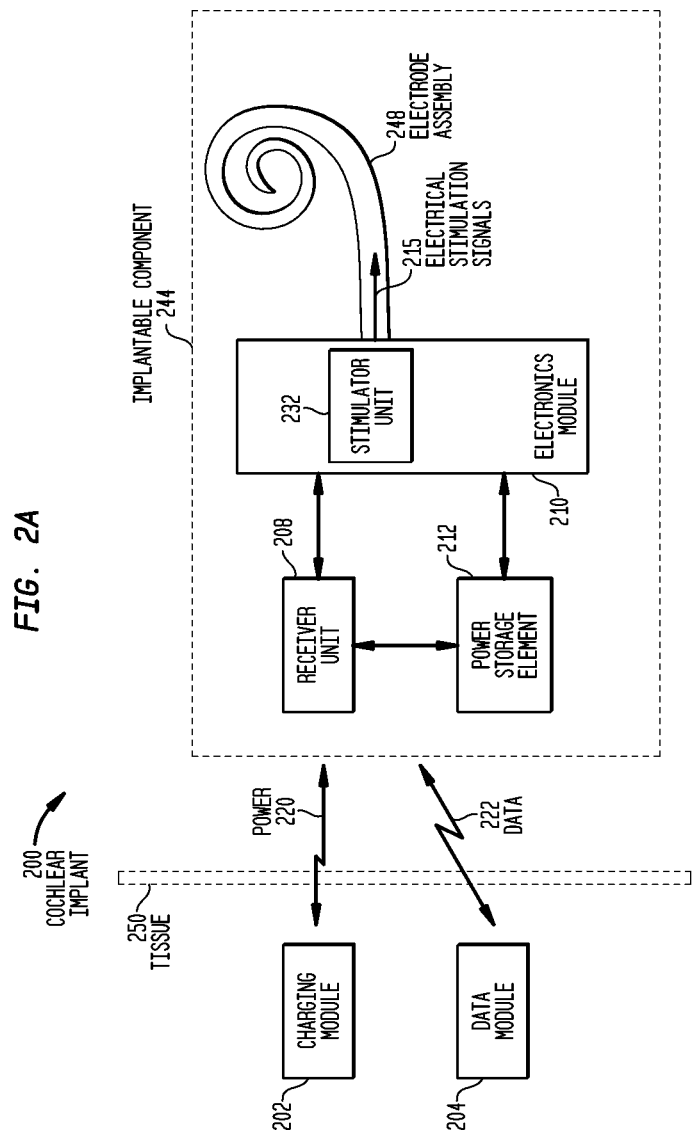
FIG. 2A is a functional block diagram of a cochlear implant, in accordance with embodiments of the present invention.

FIG. 2A is a functional block diagram of a cochlear implant 200 in accordance with embodiments of the present invention. Cochlear implant 200 comprises an implantable component 244 configured to be implanted beneath a recipient's skin or other tissue 250, a first external device 204, shown as data module 204, and a second external devices 202, shown as charging module 202. Similar to the embodiments described above with reference to FIG. 1, implantable component 244 comprises a receiver unit 208 which receives data and power from data module 204 and charging module 202, respectively. Data module 204 transmits data 222 to receiver unit 208 via a magnetic induction data link, while charging module 202 transmits power 220 to receiver unit 208 via a magnetic induction power link. The details of transmission of data and power to receiver unit 208 are provided below.

Implantable component 244 also comprises a power storage element 212, electronics module 210 and an electrode assembly 248. Power storage element 212 is configured to store power received by receiver unit 208, and to distribute power, as needed, to the elements of implantable component 244. Power storage element 212 may comprise, for example, a rechargeable battery 212.

As shown, electronics module 210 includes stimulator unit 232. Electronics module 210 may also include one or more other functional components used to generate or control delivery of electrical stimulation signals 215 to the recipient. For example, as described below, in certain embodiments, electronics module 210 may include a sound processor. As described above, electrode assembly 248 is inserted into the recipient's cochlea and is configured to deliver electrical stimulation signals 215 generated by stimulator unit 232 to the cochlea.

In certain embodiments, implantable component 244 may comprise a single unit having all components disposed in a common housing from which electrode assembly 248 extends, sometimes referred to as a stimulator/receiver unit. In other embodiments, implantable component 244 comprises a combination of several separate units communicating via wire or wireless connections. For example, battery 212 may be a separate unit.

Figure 2B:
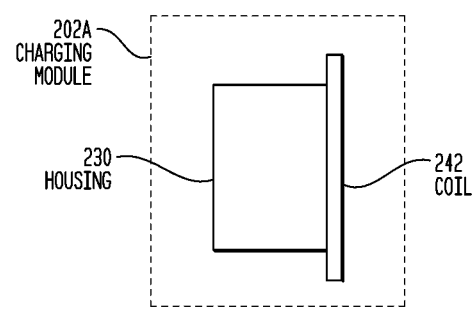
FIG. 2B is a perspective view of an exemplary charging module in accordance with embodiments of the present invention.

FIG. 2B is a perspective view of one embodiment of charging module 202 of FIG. 2A, referred to herein as charging module 202A. Charging module 202A comprises a housing 230 having a power source (not shown), a power transmitter (also not shown) and a data receiver (also not shown) positioned therein. Attached to the exterior of housing 230 is a coil 232. As described below with reference to FIG. 3A, the power transmitter provides power from the power source to implantable component 244 (FIG. 2A) via coil 242. Charging module 202A further comprises a magnet (not shown) which is configured to attach the charging module to the recipient via magnetic coupling with a magnet in implantable component 244.

Figure 2C:
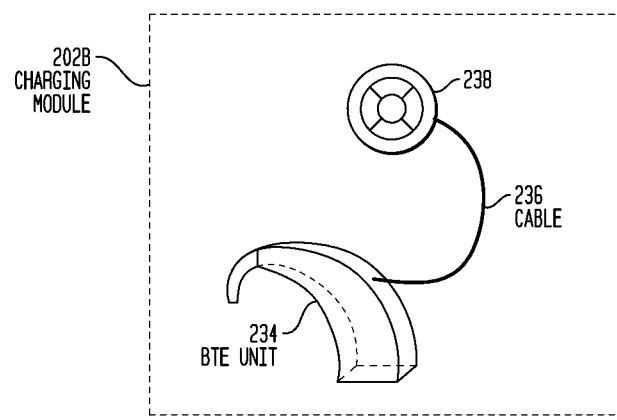
FIG. 2C is a perspective view of an exemplary charging module in accordance with embodiments of the present invention.

FIG. 2C is a perspective view an alternative embodiment of charging module 202 of FIG. 2A, referred to herein as charging module 202B. Charging module 202B comprises a housing 234 that is configured to be worn behind the ear of the recipient, referred to as behind-the-ear (BTE) unit 234. BTE unit 234 has therein a power source (not shown), a power transmitter (also not shown) and a data receiver (also not shown). Connected to the power transmitter via a cable 236 is a coil 238. As described below with reference to FIG. 3A, the power transmitter provides power from the power source to implantable component 244 (FIG. 2A) via coil 238.

Figure 3A:
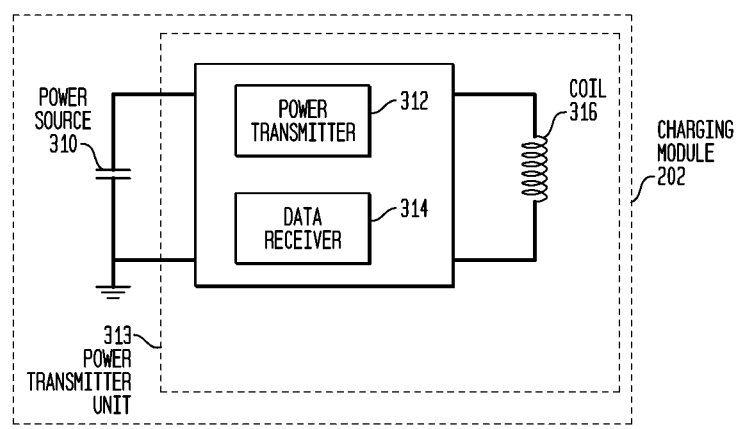
FIG. 3A is a simplified schematic diagram of a charging module in accordance with embodiments of the present invention.

FIG. 3A is a simplified schematic diagram of charging module 202 in accordance with embodiments of the present invention. As noted, charging module 202 comprises a power source 310 and a power transmitter unit 313. As shown, power transmitter unit 313 includes a power transmitter 312, a data receiver 314 and a coil 316.

Coil 316 is a wire antenna coil comprised of multiple turns of electrically insulated single-strand or multi-strand platinum or gold wire. Power transmitter 312 comprises circuit components which inductively transmit power from power source 310 via coil 316 to implantable component 244 (FIG. 2A). Data receiver 314 comprises circuit components which receive via coil 316 inductively transmitted data from one or more other components of cochlear implant 200, such as data module 204 (FIG. 2A). For ease of description, power transmitter 312 and data receiver 314 are shown separate. However, it should be appreciated that in certain embodiments, at least some of the components of receiver 314 may be used to transmit power.

Figure 3B:
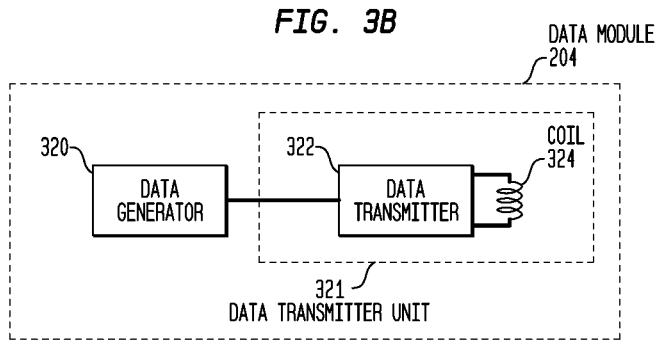
FIG. 3B is a simplified schematic diagram of a data module in accordance with embodiments of the present invention.

FIG. 3B is a simplified schematic diagram of data module 204 in accordance with embodiments of the present invention. Data module 204 comprises a data generator 320 and data transmitter unit 321. Data transmitter unit 321 comprises a data transmitter 322 and a coil 324. Coil 324 is a wire antenna coil comprised of multiple turns of electrically insulated single-strand or multi-strand platinum or gold wire.

Data generator 320 comprise functional elements which cooperate to output data for transmission to implantable component 244 (FIG. 2A). In certain embodiments, data generator 320 comprises a sound input element, such as a microphone, which receives a sound. The microphone outputs electrical signals representative of the received sound which are then transmitted by data transmitter 322 via coil 324 to implantable component 244. It would be appreciated that a sound input element in accordance with embodiments of the present invention may comprise an electrical input which connects cochlear implant 200 for example, FM hearing systems, MP3 players, televisions, mobile phones, etc. In an alternative embodiment, data generator 320 comprises a sound input element, as described above, and a sound processor configured to convert the microphone output into encoded data signals which may be transmitted to implantable component 244.

Data module 204 may comprise any number of components which transmit data to implantable component 204. For example, data module 204 may comprise an external remote control, and external fitting system, a behind-the-ear (BTE) device having one or of a microphone or sound processor therein, an in-the-ear device, etc. The embodiments of data module 204 are provided for illustrative purposes and should not be considered limiting.

Figure 3C:
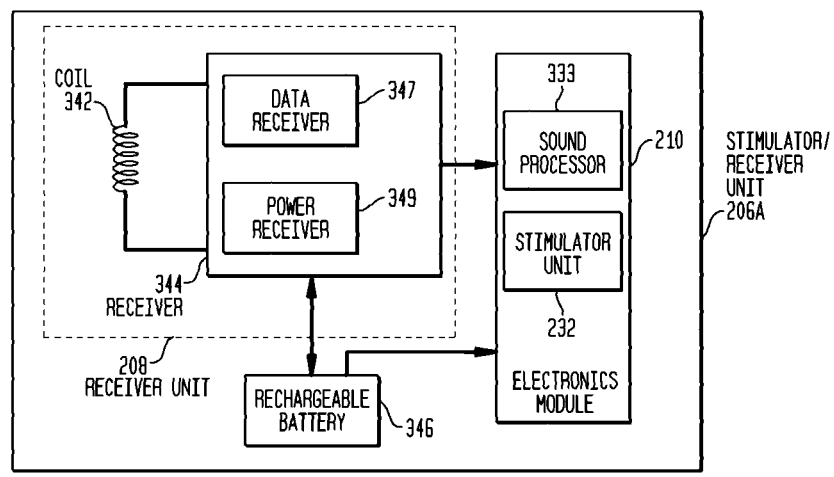
FIG. 3C is a simplified schematic diagram of an implantable component in accordance with embodiments of the present invention.

FIG. 3C is a simplified schematic diagram of one embodiment of implantable component 244 of FIG. 2A, referred to as implantable component 244A. Implantable component 244A comprises a receiver unit 208, a power storage element, shown as rechargeable battery 346, and electronics module 210. Receiver unit 208 includes a coil 342 and a receiver 344. Receiver 344 comprises circuit components which receive via coil 342 inductively transmitted data and power from other components of cochlear implant 200, such as data module 204 and charging module 202 (FIG. 2A). The components for receiving data and power are shown in FIG. 3C as data receiver 347 and power receiver 349. For ease of description, data receiver 347 and power receiver 349 are shown separate. However, it should be appreciated that in certain embodiments, at least some of the components of receiver 344 may be used to receive both power and data.

In the illustrative embodiments of the present invention, receiver unit 208, power transmitter unit 313, and data transmitter unit 321 establish a transcutaneous communication link over which data and power is transferred from data module 204 and charging module 202, respectively, to implantable component 244A. As shown, the transcutaneous communication link comprises a magnetic induction link having one receiving coil 342.

The transcutaneous communication link established by receiver unit 208, power transmitter unit 313 and data transmitter unit 321 uses time interleaving of power and data on a single frequency channel or band to transmit the power and data to implantable component 244. The time interleaving uses successive time frames, each having a time length and each divided into two or more time slots. Within each frame, one or more time slots are allocated to power transmitter unit 313, while one or more time slots are allocated to data transmitter unit 321. Data transmitter unit 321 and power transmitter unit 313 are configured to transmit data and power, respectively, to implantable component 244 within their allocated time slots within each frame. The allocation of time slots to the different transmitters and the coordination of transfer of power and data are described in greater detail below.

The power received by receiver unit 208 is provided to rechargeable battery 346 for storage and distribution, as needed, to elements of implantable component 244A. As shown, electronics module 210 includes stimulator unit 232, and may also include one or more other functional components used to generate or control delivery of electrical stimulation signals to the recipient. In the specific embodiment of FIG. 3C, electronics module 210 includes a sound processor 333.

As shown, comprises a receiver unit 208, rechargeable battery 346A and electronics module 210 are integrated in a single implantable housing, referred to as stimulator/receiver unit 206A. It would be appreciated that in alternative embodiments, implantable component 244 may comprise a combination of several separate units communicating via wire or wireless connections.

Figure 3D:
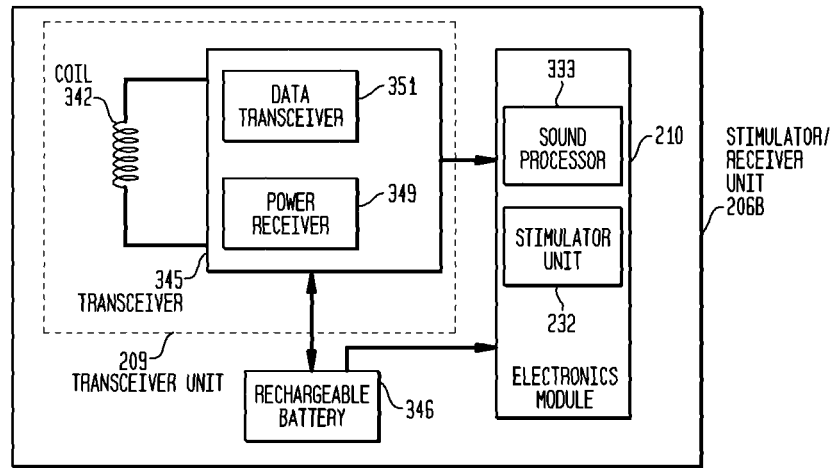
FIG. 3D is a simplified schematic diagram of an implantable component in accordance with embodiments of the present invention.

FIG. 3D is a simplified schematic diagram of an alternative embodiment of implantable component 244 of FIG. 2A, referred to as implantable component 244B. Implantable component 244B comprises a transceiver unit 209, a power storage element, shown as rechargeable battery 346 and electronics module 210. Transceiver unit 209 includes a coil 342 and a transceiver 345. Transceiver 345 comprises circuit components which receive via coil 342 inductively transmitted data and power from other components of cochlear implant 200, such as data module 204 and charging module 202 (FIG. 2A). Transceiver 345 also includes components which transmit data via coil 342 to other components of cochlear implant 200. As shown, transceiver 346 comprises a data transceiver 351 configured to receive and transmit data, as well as a power receiver 349. For ease of description, data transceiver 351 and power receiver 349 are shown separate. However, it should be appreciated that in certain embodiments, at least some of the same components of transceiver 345 may be used to receive power and receive or transmit data.

Similar to the embodiments described above with reference to FIG. 3C, transceiver unit 209, power transmitter unit 313 and data transmitter unit 321 establish a transcutaneous communication link over which data and power is transferred from data module 204 and charging module 202, respectively, to implantable component 244B. As shown, the transcutaneous communication link comprises a magnetic induction link having one receiving coil 342. Similar to the embodiments described above, the transcutaneous communication link established by transceiver unit 209, power transmitter unit 313 and data transmitter unit 321 uses time interleaving of power and data on a single frequency channel to transmit the power and data to implantable component 244.

The time interleaving uses successive time frames, each having a time length and each divided into two or more time slots. Within each frame, one or more time slots are allocated to power transmitter unit 313, while one or more time slots are allocated to data transmitter unit 321. Data transmitter unit 321 and power transmitter unit 313 are configured to transmit data and power, respectively, to implantable component 244 within their allocated time slots within each frame.

In certain embodiments of the present invention, one or time slots within a frame may be allocated to transceiver unit 209. During its allocated time slot(s) transceiver unit 209 transmits data to one or more components of cochlear implant 200. The allocation of time slots to the transmitters and/or transceiver, and the coordination of transfer of power and data are described in greater detail below.

The power received by transceiver unit 209 is provided to rechargeable battery 346 for storage and distribution, as needed, to elements of implantable component 244B. Similar to the embodiments of FIG. 3C, electronics module 210 includes stimulator unit 232 and a sound processor 333. As shown, comprises a transceiver unit 209, rechargeable battery 346 and electronics module 210 are integrated in a single implantable housing, referred to as stimulator/receiver unit 206B. It would be appreciated that in alternative embodiments, implantable component 244B may comprise a combination of several separate units communicating via wire or wireless connections.

As noted above, embodiments of the present invention transmit power and data over a transcutaneous communication link implementing a time interleaving scheme. As used herein, a time interleaving scheme is a channel access protocol in which two or more devices share a common or overlapping frequency channel band. The scheme includes successive time frames which are each divided into two or more time slots. The two or more devices are each allocated time slots within each frame for transmission of data or power. An exemplary time interleaving scheme is sometimes referred to as a time division multiple access (TDMA) scheme.

Figure 4A:
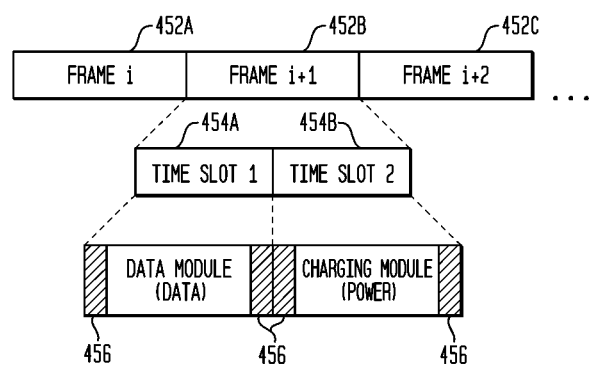
FIG. 4A is a diagram illustrating successive frames and time slots of an interleaving scheme in accordance with embodiments of the present invention.
Figure 4B:
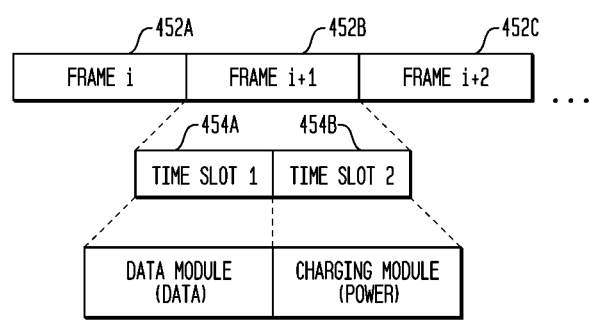
FIG. 4B is a diagram illustrating successive frames and time slots of an interleaving scheme in accordance with embodiments of the present invention.

FIGS. 4A-4E are diagrams illustrating how exemplary time interleaving schemes of the present invention may be implemented. As shown in FIGS. 4A and 4B, the time interleaving scheme comprises successive time frames 452. In these embodiments, each time frame 452 has a fixed time length and is divided into two time slots, schematically shown as time slots 454A and 454B. As described above, time slots 454 are each allocated to a device which is configured to transmit power or data. In the embodiments of FIGS. 4A and 4B, the first time slot in each frame, time slot 454A, is allocated to a data transmitter in data module 204 (FIG. 2A) which transmits data within the time slot. The second time slot in each frame, time slot 454B, is allocated to a power transmitter within charging module 202 (FIG. 2A) which transmits data within the time slot.

Within the time interleaving scheme of the present invention, data or power is only transmitted for a portion of a time slot. In other words, portions of each time slot remain vacant or unoccupied. This is shown as unoccupied portions 456 at the beginning and end of each time slot. For ease of illustration, the unoccupied portions are not shown in FIGS. 4B-4E.

The unoccupied portions 456 are provided because it may be difficult to ensure that different transmitters transmit power or data at the exact time required to prevent collisions. Therefore, unoccupied portions 456 provide a buffer zone to further prevent collisions and interference.

As would be appreciated, the unoccupied portions 456 limit the potential bandwidth of the frequency channel over which data and power is provided. This may be a problem in systems which require extremely large bandwidth to transmit large amounts of data. However, this is not a problem for implantable medical devices because such devices typically do not have a need to transfer large amounts of data quickly. Therefore, bandwidth considerations are not as important in implantable medical devices, as in, for example, cellular systems.

As noted above, FIGS. 4A and 4B are embodiments of the present invention in which the successive frames are divided into two time slots in which one time slot is allocated to each of data module 204 and charging module 202. In certain embodiments of the present invention, the time slots in each of the successive frames are allocated to each of data module 204 and charging module 202 prior to the transmission of the power and data. That is, the time slots are allocated in a predetermined manner. In these embodiments, the data module 204 and charging module 202 transmit in the same order within each successive frame.

In alternative embodiments of the present invention, the time slots may be allocated dynamically to each of data module 204 and charging module 202. That is, the allocation of time slots is performed in real-time based on one or conditions existing in the cochlear implant. In certain such embodiments, a scheduling algorithm may be provided to dynamically allocate a variable number of time slots in each frame for data or power. The algorithm may make the dynamic allocation based on the power demands of the implantable component, or the need to transfer a large amount of data. For example, in one such embodiment, the implant could determine that is necessary to transfer additional power. As such, in one or more of the successive frames, both time slots could be allocated to charging module 202. Alternatively, the implant could determine that is necessary to transfer a large amount of data. In this embodiment, in one or more of the successive frames, both time slots could be allocated to data module 204.

The above uneven allocation between data module 204 and charging module 204 may also be predetermined prior to transmission based on, for example, the state of the cochlear implant. For example, the implant could determine that the charging module is turned off or has been removed, thus there is no need to transfer power. Therefore, the cochlear implant could allocate all time slots to data module 204 until the presence of charging module 202 is detected. In such embodiments, charging module 202 could be configured to transmit a signal indicating its presence to, for example, data module 204.

The ability to allocate time slots dynamically provides the implantable medical device with the unique ability to adjust to the power/data demands of the device in real-time. This real-time adjustment ability is lacking from conventional systems.

Figure 4C:
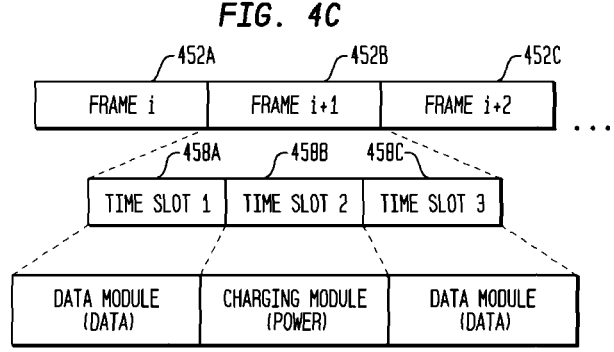
FIG. 4C is a diagram illustrating successive frames and time slots of an interleaving scheme in accordance with embodiments of the present invention.
Figure 4D:
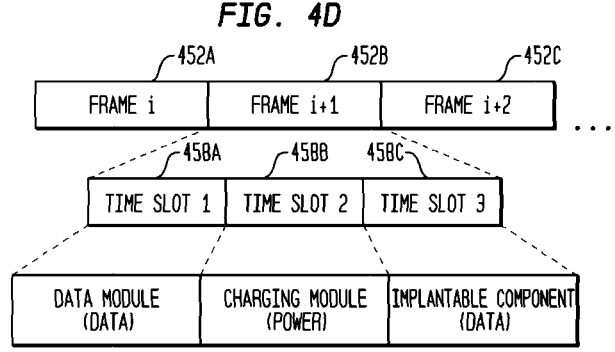
FIG. 4D is a diagram illustrating successive frames and time slots of an interleaving scheme in accordance with embodiments of the present invention.
Figure 4E:
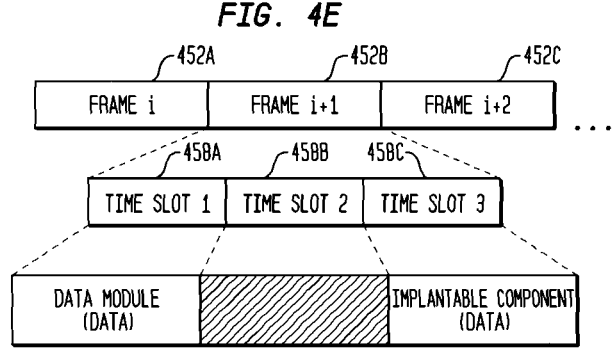
FIG. 4E is a diagram illustrating successive frames and time slots of an interleaving scheme in accordance with embodiments of the present invention.

As shown in FIGS. 4C-4E, the time interleaving scheme comprises successive time frames 452. In these embodiments, each time frame 452 has a fixed time length and is divided into three time slots, schematically shown as time slots 458A, 458B and 458C. As described above, time slots 458 may be allocated to a device which is configured to transmit power or data.

In the embodiments of FIG. 4C, the first time slot in each frame, time slot 458A, is allocated to a data transmitter in data module 204 (FIG. 2A) which transmits data within the time slot. The second time slot in each frame, time slot 458B, is allocated to a power transmitter within charging module 202 (FIG. 2A) which transmits data within the time slot. The third time slot in each frame is also allocated to data module 204. Therefore, data module 204 transmits twice within each successive frame.

In the embodiments of FIG. 4D, the first time slot in each frame, time slot 458A, is allocated to a data transmitter in data module 204 (FIG. 2A) which transmits data within the time slot. The second time slot in each frame, time slot 458B, is allocated to a power transmitter within charging module 202 (FIG. 2A) which transmits data within the time slot. The third time slot in each frame is also allocated to a transceiver unit 209 within implantable component 244. In this embodiment, transceiver unit 209 within implantable component transmits data to, for example, data module 204, thereby providing bi-directional transfer of data within the transcutaneous communication link. These embodiments are described below with reference to FIG. 5B.

In the embodiments of FIG. 4E, the first time slot in each frame, time slot 458A, is allocated to a data transmitter in data module 204 (FIG. 2A) which transmits data within the time slot. The second time slot 458B is unoccupied, while the third time slot in each frame is allocated to a transceiver unit 209 within implantable component 244. In this embodiment, transceiver unit 209 within implantable component transmits data to, for example, data module 204, thereby providing bi-directional transfer of data within the transcutaneous communication link. These embodiments are described below with reference to FIG. 5B.

The embodiments of FIG. 4E represent the situation when charging module 202 is turned off or has been removed, thus there is no need to transfer power. In such embodiments, charging module 202 could be configured to transmit a signal indicating its presence to, for example, data module 204.

More specifically, one or more other components of the cochlear implant could make use of the charging module timeslot when the charging module is not present or deactivated. Specifically, because charging typically only occurs a few hours a day, the cochlear implant could detect presence of the charging module and make an optimal arrangement of time slot allocation based on the presence, or absence of, the charging module. This detection could be based on RF signal strength measurement or/and RF signal shape. In certain such embodiments, the implantable component could function as a network controller that provides the desired frame and time slot structure to all other devices.

As detailed above, the time slots in each of the successive frames are allocated to each of data module 204, charging module 202 and/or implantable component 244 prior to the transmission of the power and data. That is, the time slots are allocated in a predetermined manner. In certain such embodiments, the data module 204 and charging module 202 transmit in the same order within each successive frame.

In alternative embodiments of the present invention, the time slots may be allocated dynamically to each of data module 204, charging module 202 and/or implantable component 244. That is, the allocation of time slots is performed in real-time based on one or conditions existing in the cochlear implant. In certain such embodiments, a scheduling algorithm may be provided to dynamically allocate a variable number of time slots in each frame for data or power. The algorithm may make the dynamic allocation based on the power demands of the implantable component, or the need to transfer a large amount of data.

For example, in one such embodiment, the implant could determine that is necessary to transfer additional power. As such, in one or more of the successive frames, two or more time slots could be allocated to charging module 202. This would reduce the data transfer rate, but would reduce the charging time. Alternatively, data module 204 could determine that is necessary to transfer a large amount of data to the implantable component. In this embodiment, in one or more of the successive frames, two or more time slots could be allocated to data module 204. As noted above, this uneven allocation between data module 204 and charging module 204 may also be predetermined prior to transmission based on, for example, the state of the cochlear implant.

The ability to allocate time slots dynamically provides the implantable medical device with the unique ability to adjust to the power/data demands of the device in real-time. This real-time adjustment ability is lacking from conventional systems.

The time interleaving scheme of present invention provides that the charging module 204, data module 202 and/or implantable component 244 only needs to transmit during its allocated time slot. Therefore, at all other times, the transmitters/receivers may perform various other functions, such as ensuring synchronization of the transmission of power and data to prevent collisions and interference.

The time interleaving scheme of the present invention is particularly applicable to implantable medical devices due to the sharing of a common frequency channel. This provides for a simplified implantable component because a single receiver coil may be shared for both power and data. Such multi-purpose single strands of would coil add simplicity to the system. This is different than convention cochlear implants which use separate power and data communication paths. Similarly, the non-continuous transmission of data and power provides for manageable synchronization between the various transmitters that does not require large amounts of additional communication between the different devices.

FIGS. 4A-4E have illustrated frames have time slots of the substantially identical time length. It would be appreciated that time slots of varying time lengths may also be used within each frame. In certain embodiments, the length of the slots may be fixed, or one or more time slots may have a dynamically changing length.

Figure 5A:
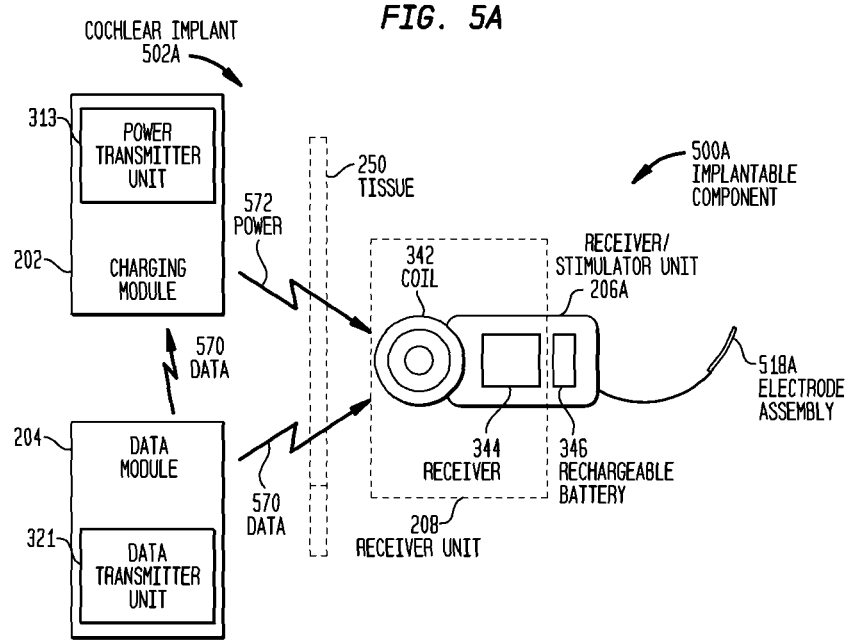
FIG. 5A is a schematic block diagram of a cochlear implant in accordance with one embodiment of the present invention.

FIG. 5A is a schematic block diagram of cochlear implant 502A in accordance with one embodiments of the present invention. Cochlear implant 502A comprises an external or non-implantable charging module 202 implemented as described above, an external data module 204 implemented as described above, and an implantable component 500A. Implantable component 500A is configured to be implanted under the skin or tissue 250 of a recipient.

Implantable component 500A comprises a receiver/stimulator unit 206A having, as described above, a receiver unit 208, a rechargeable battery 346 and an electronics module (FIG. 3C) therein. Implantable component 500B further comprises an electrode assembly 518A to deliver stimulation signals to the recipient. For ease of illustration, the electronics module is omitted from FIG. 5A.

Also as described above, receiver unit 208 has a receiver 344 and a coil 342 therein. As shown above with reference to FIG. 3B, data module comprises a data transmitter unit 321 configured to inductively transmit data 570 to receiver unit 208. Data 570 is transmitted, for example, via a weakly coupled magnetic induction link. Furthermore, as described above with reference to FIG. 3A, charging module 202 comprises a power transmitter unit 313 configured to transmit power 572 to receiver unit 208. Power 572 is transmitted via a closely-coupled magnetic induction link operating in the reactive near field. The magnetic induction power and data links operate at radio frequencies (RF).

As described above, receiver unit 208, power transmitter unit 313, and data transmitter unit 321 are configured to establish a transcutaneous communication link in which data and power is inductively transmitted from data transmitter unit 321 and power transmitter 313, respectively, to receiver unit 208. The transcutaneous communication link, represented by arrows 570 and 572, uses time interleaving of power and data on a single frequency channel or band to transmit the power and data to receiver unit 208. As noted, the time interleaving uses successive time frames, each having a time length and each divided into two or more time slots. Within each frame, one or more time slots are allocated to power transmitter unit 313, while one or more time slots are allocated to data transmitter unit 321. Data transmitter unit 321 and power transmitter unit 313 are configured to transmit data and power, respectively, to implantable component 244 within their allocated time slots within each frame.

In the illustrative embodiments of FIG. 5A, the time interleaving scheme comprises successive frames each divided into two time slots. Within each frame, the first time slot is allocated to data transmitter unit 321. During this first time slot of each frame, data 570 is inductively transmitted by unit 321 to receiver unit 208. The second time slot within the successive frames is allocated to power transmitter 313. During this second time slot of each frame, power 572 is inductively transmitted by unit 313 to receiver unit 208.

As shown in FIG. 5A, data 570 transmitted by data transmitter unit 321 is also received by a data receiver 314

(shown in FIG. 3A) within power transmitter 313. The data received by receiver 314 is used by power transmitter unit 313 to synchronize the transmission of power 572 within time slots allocated to unit 313. For example, in embodiments of the present invention, data module 214 includes the system clock used to control the timing of data and power within the transcutaneous communication link. The transmitted data 570 may include a timing reference that enables power transmitter unit 313 to remain synchronized with the system clock. This synchronization prevents collisions between transmitted data and power.

As would be appreciated, any device within cochlear implant 502A having a power or data transmitter unit can operate within the transcutaneous communication link. As shown in FIG. 5A, the system clock to provide a common time base is provided by an external data module, for example, a behind the ear (BTE) or an in the ear device. It would be further appreciated that the charging module or the implantable component, if properly configured to transmit data, could include the system clock to provide the common time base.

The first and second time slots may be allocated to power transmitter unit 313 and data transmitter unit 321 as described above with reference to FIGS. 4A-4E. For example, as described above, the first and second time slots may be allocated in a predetermined manner prior to transmitting, dynamically in real time, etc.

In certain embodiments of the present invention, power transmitter unit 313 is configured to verify that a time slot allocated thereto is unoccupied prior to transmitting power within the time slot. That is, the power transmitter unit 313 waits for confirmation that a time slot is available prior to transmitting power. This confirmation may be provided by information received from data transmitter unit 321.

Figure 5B:
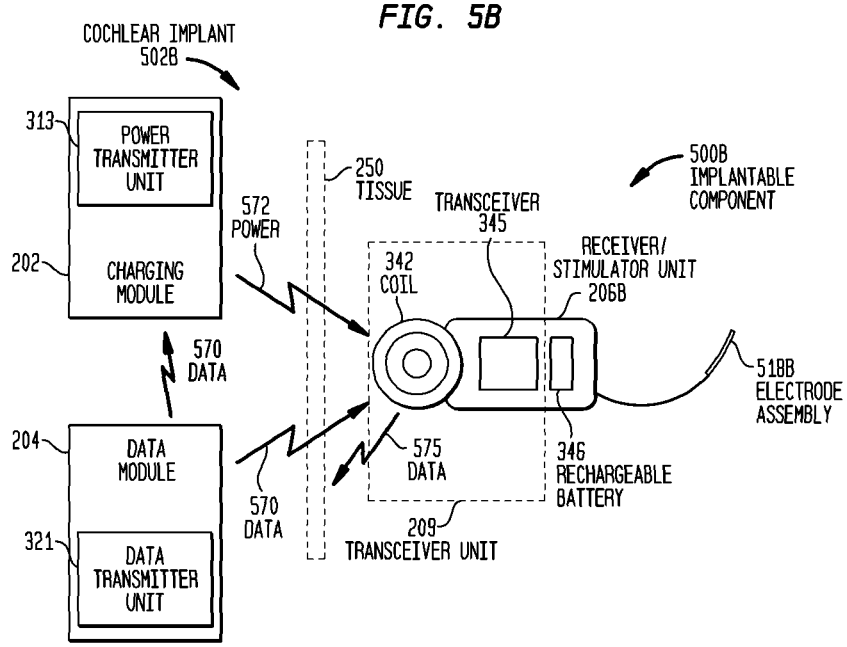
FIG. 5B is a schematic block diagram of a cochlear implant in accordance with one embodiment of the present invention.

FIG. 5B is a schematic block diagram of cochlear implant 502B in accordance with one embodiments of the present invention. Cochlear implant 502B comprises an external or non-implantable charging module 202 implemented as described above, an external data module 204 implemented as described above, and an implantable component 500B. Implantable component 500B is configured to be implanted under the skin or tissue 250 of a recipient.

Implantable component 500B comprises a receiver/stimulator unit 206B having, as described above, a transceiver unit 209, a rechargeable battery 346 and an electronics module (FIG. 3D) therein. For ease of illustration, the electronics module is omitted from FIG. 5B. Implantable component 500B further comprises an electrode assembly 518B to deliver stimulation signals to the recipient.

Also as described above, transceiver unit 209 has a transceiver 345 and a coil 342 therein. As shown above with reference to FIG. 3B, data module comprises a data transmitter unit 321 configured to inductively transmit data to transceiver unit 209. Furthermore, as described above with reference to FIG. 3A, charging module 202 comprises a power transmitter unit 313 configured to transmit power to transceiver unit 209.

As described above, transceiver unit 209, power transmitter unit 313, and data transmitter unit 321 are configured to establish a transcutaneous communication link in which data and power is inductively transmitted from data transmitter unit 321 and power transmitter 313, respectively, to transceiver unit 209. The transcutaneous communication link, represented by arrows 570 and 572, uses time interleaving of power and data on a single frequency channel to transmit the power and data to transceiver unit 209. As noted, the time interleaving uses successive time frames, each having a time length and each divided into two or more time slots. Within each frame, one or more time slots are allocated to power transmitter unit 313, while one or more time slots are allocated to data transmitter unit 321. Data transmitter unit 321 and power transmitter unit 313 are configured to transmit data and power, respectively, to implantable component 244 within their allocated time slots within each frame.

In the illustrative embodiments of FIG. 5B, transcutaneous communication link comprises a bi-directional communication link in which data 575 may be transferred from transceiver unit 209 to, for example, data transmitter unit 321. In this case, data transmitter unit 321 comprises a data receiver to receive data 575. Because in this exemplary embodiment three devices are configured to transmit on the transcutaneous communication link, the time interleaving scheme comprises successive frames each divided into three time slots. Within each frame, one time slot is allocated to data transmitter unit 321. During this first time slot of each frame, data 570 is inductively transmitted by unit 321 to transceiver unit 209. A second time slot within the successive frames is allocated to power transmitter 313. During this second time slot of each frame, power 572 is inductively transmitted by unit 313 to transceiver unit 209. A third time slot is allocated to transceiver unit 209. During this third time slot of each frame, data 575 is inductively transmitted by transceiver unit 209 to data transmitter unit 321.

As shown in FIG. 5B, data 570 transmitted by data transmitter unit 321 is received by a data receiver 314 (shown in FIG. 3A) within power transmitter 313, and by transceiver unit 209. Transmitted data 570 is used by power transmitter unit 313 and transceiver unit 209 to synchronize the transmission of power 572 and data 575 within allocated time slots. For example, in embodiments of the present invention, data module 214 includes the system clock used to control the timing of data and power within the transcutaneous communication link. The transmitted data 570 may include a timing reference that enables power transmitter unit 313 and transceiver unit 209 to remain synchronized with the system clock. This synchronization prevents collisions between transmitted data 570, 575 and power 572.

As would be appreciated, any device within cochlear implant 502B having a power or data transmitter unit can operate within the transcutaneous communication link. As shown in FIG. 5B, the system clock to provide a common time base is provided by an external data module, for example, a behind the ear (BTE) or an in the ear device. It would be further appreciated that the charging module or the implantable component, if properly configured to transmit data, could include the system clock to provide the common time base.

The first, second and third time slots may be allocated to power transmitter unit 313, data transmitter unit 321 and transceiver unit 209 as described above with reference to FIGS. 4A-4E. For example, as described above, the first, second time and third time slots may be allocated in a predetermined manner prior to transmitting, dynamically in real time, etc.

In certain embodiments of the present invention, power transmitter unit 313 and/or transceiver unit 209 is configured to verify that a time slot allocated thereto is unoccupied prior to transmitting power within the time slot. That is, the power transmitter unit 313 and/or transceiver unit 209 waits for confirmation that a time slot is available prior to transmitting power. This confirmation may be provided by information received from data transmitter unit 321.

FIG. 5C is a schematic block diagram of a cochlear implant 504A in accordance with one embodiment of the present invention. As shown, cochlear implant 504A is a bilateral cochlear implant having a first implantable component 500A implantable in a first ear of the recipient's ear. First implantable component 500A is implemented as described above with reference to FIG. 5A. Specifically, as noted, implantable component 500A comprises a receiver/stimulator unit 206A having receiver unit 208 and rechargeable battery 346 therein. Implantable component 500A further comprises electrode assembly 518A insertable into a first cochlea of the recipient.

Bilateral cochlear implant 504A further comprises a second implantable component 500B implantable in a second ear of the recipient. Implantable component 500B is implemented as described above with reference to FIG. 5B. Specifically, as noted above, implantable component 500B comprises a receiver/stimulator unit 206B having transceiver unit 209 and rechargeable battery 346 therein. Implantable component 500B further comprises electrode assembly 518B insertable into a second cochlea of the recipient.

As shown, bilateral cochlear implant 504A comprises a data module 204 positioned proximate to the second ear in which second implantable component 500B is implanted. Data module 204 comprises a data transmitter unit 321 configured to inductively transmit data to transceiver unit 209. Bilateral cochlear implant 504A further comprises a charging module 202 positioned proximate to the first ear in which first implantable component 500A is implanted. Charging module 202 comprises a power transmitter unit 313 configured to transmit power to receiver unit 208.

Transceiver unit 209, receiver unit 208, power transmitter unit 313, and data transmitter unit 321 are configured to establish a transcutaneous communication link in which data and power is inductively transmitted. In the illustrative embodiments, data 576 is transmitted from data transmitter unit 321 to transceiver unit 209, while power is transmitted from power transmitter 313 to receiver unit 208. As would be appreciated, a second charging module may also be included to transmit power to transceiver unit 209. However, for ease of illustration this second charging module is not shown.

The transcutaneous communication link, represented by arrows 576 and 572, uses time interleaving of power and data on a single frequency channel to transmit the power and data to receiver unit 208 and transceiver unit 209, respectively. As noted, the time interleaving uses successive time frames, each having a time length and each divided into two or more time slots. Within each frame, one or more time slots are allocated to power transmitter unit 313, while one or more time slots are allocated to data transmitter unit 321. Data transmitter unit 321 and power transmitter unit 313 are configured to transmit data and power, respectively, within their allocated time slots.

Because in this exemplary embodiment two devices are configured to transmit on the transcutaneous communication link, the time interleaving scheme comprises successive frames each divided into two time slots. Within each frame, one time slot is allocated to data transmitter unit 321. During this first time slot of each frame, data 576 is inductively transmitted by unit 321 to transceiver unit 209. A second time slot within the successive frames is allocated to power transmitter 313. During this second time slot of each frame, power 572 is inductively transmitted by unit 313 to receiver unit 208.

In certain embodiments of the present invention, data 576 transmitted by data transmitter unit 321 may be received by a data receiver 314 (shown in FIG. 3A) within power transmitter 313. In these embodiments, transmitted data 576 is used by power transmitter unit 313 to synchronize the transmission of power 572 within allocated time slots. For example, in embodiments of the present invention, data module 214 includes the system clock which provides a common time base for the transfer of data and power within the transcutaneous communication link. Transmitted data 576 may include a timing reference that enables power transmitter unit 313 to remain synchronized with the system clock. This synchronization prevents collisions between transmitted data 576 and power 572.

The first and second time slots may be allocated to power transmitter unit 313 and data transmitter unit 321 as described above with reference to FIGS. 4A-4E. For example, as described above, the first and second time slots may be allocated in a predetermined manner prior to transmitting, dynamically in real time, etc.

FIG. 5D is a schematic block diagram of a cochlear implant 504B in accordance with one embodiment of the present invention. As shown, cochlear implant 504B is a bilateral cochlear implant having a first implantable component 500A implantable in a first ear of the recipient's ear. First implantable component 500A is implemented as described above with reference to FIG. 5A. Specifically, as noted, implantable component 500A comprises a receiver/stimulator unit 206A having receiver unit 208 and rechargeable battery 346 therein. Implantable component 500A further comprises electrode assembly 518A insertable into a first cochlea of the recipient.

Bilateral cochlear implant 504B further comprises a second implantable component 500B implantable in a second ear of the recipient. Implantable component 500B is implemented as described above with reference to FIG. 5B. Specifically, as noted above, implantable component 500B comprises a receiver/stimulator unit 206B having transceiver unit 209 and rechargeable battery 346 therein. Implantable component 500B further comprises electrode assembly 518B insertable into a second cochlea of the recipient.

As shown, bilateral cochlear implant 504B comprises a data module 204 positioned proximate to the first ear in which first implantable component 500B is implanted. Data module 204 comprises a data transmitter unit 321 configured to inductively transmit data 570 to receiver unit 208. Bilateral cochlear implant 504B further comprises a charging module 202 positioned proximate to the first ear in which first implantable component 500A is implanted. Charging module 202 comprises a power transmitter unit 313 configured to transmit power to receiver unit 208. Furthermore, transceiver unit 209 is configured to transmit data 578 to receiver unit 208. As would be appreciated, a second charging module may also be included to transmit power to transceiver unit 209. However, for ease of illustration this second charging module is not shown.

Transceiver unit 209, receiver unit 208, power transmitter unit 313, and data transmitter unit 321 are configured to establish a transcutaneous communication link in which data and power is inductively transmitted from three sources to receiver unit 208. The transcutaneous communication link, represented by arrows 570, 572 and 578 uses time interleaving of power and data on a single frequency channel to transmit the power and data to receiver unit 208. As noted, the time interleaving uses successive time frames, each having a time length and each divided into two or more time slots. Within each frame, one or more time slots are allocated to power transmitter unit 313, one or more time slots are allocated to data transmitter unit 321 and one or more time slots are allocated to transceiver unit 209. Data transmitter unit 321, power transmitter unit 313 and transceiver unit 209 are configured to transmit data and power, respectively, within their allocated time slots.

Because in this exemplary embodiment three devices are configured to transmit on the transcutaneous communication link, the time interleaving scheme comprises successive frames each divided into three time slots. Within each frame, one time slot is allocated to data transmitter unit 321. During this first time slot of each frame, data 570 is inductively transmitted by unit 321 to receiver unit 208. A second time slot within the successive frames is allocated to power transmitter 313. During this second time slot of each frame, power 572 is inductively transmitted by unit 313 to receiver unit 208. A third time slot within the successive frames is allocated to transceiver unit 209. During this third time slot of each frame, data 578 is inductively transmitted by transceiver unit 209 to receiver unit 208.

In certain embodiments of the present invention, data 570 transmitted by data transmitter unit 321 may be received by a data receiver 314 (shown in FIG. 3A) within power transmitter 313. This data may also be received by transceiver unit 209. For ease of illustration, the data received by transceiver unit 209 is not shown. In these embodiments, transmitted data 570 is used by power transmitter unit 313 and transceiver unit 209 to synchronize the transmission of power 572 and data 578 within allocated time slots. For example, in embodiments of the present invention, data module 214 includes the system clock which provides a common time base for the transfer of data and power within the transcutaneous communication link. Transmitted data 570 may include a timing reference that enables power transmitter unit 313 and transceiver unit 209 to remain synchronized with the system clock. This synchronization prevents collisions between transmitted data 570, 578 and power 572.

The first, second and third time slots may be allocated to power transmitter unit 313, data transmitter unit 321 and transceiver unit 209 as described above with reference to FIGS. 4A-4E. For example, as described above, the first and second time slots may be allocated in a predetermined manner prior to transmitting, dynamically in real time, etc.

FIG. 5E is a schematic block diagram of a cochlear implant 504C in accordance with one embodiment of the present invention. As shown, cochlear implant 504C is a bilateral cochlear implant having a first implantable component 500A implantable in a first ear of the recipient's ear. First implantable component 500A is implemented as described above with reference to FIG. 5A. Specifically, as noted, implantable component 500A comprises a receiver/stimulator unit 206A having receiver unit 208 and rechargeable battery 346 therein. Implantable component 500A further comprises electrode assembly 518A insertable into a first cochlea of the recipient.

Bilateral cochlear implant 504C further comprises a second implantable component 500B implantable in a second ear of the recipient. Implantable component 500B is implemented as described above with reference to FIG. 5B. Specifically, as noted above, implantable component 500B comprises a receiver/stimulator unit 206B having transceiver unit 209 and rechargeable battery 346 therein. Implantable component 500B further comprises electrode assembly 518B insertable into a second cochlea of the recipient.

As shown, bilateral cochlear implant 504C comprises a data module 204 positioned proximate to the first ear in which first implantable component 500B is implanted. Data module 204 comprises a data transmitter unit 321 configured to inductively transmit data 570 to receiver unit 208. Data transmitter 321 is also configured to transmit data 578 to transceiver unit 209. As explained below, data 578 may be the same or different data as data 570. Bilateral cochlear implant 504C further comprises a charging module 202 positioned proximate to the first ear. Charging module 202 comprises a power transmitter unit 313 configured to transmit power 572 to receiver unit 208. As would be appreciated, a second charging module may also be included to transmit power to transceiver unit 209. However, for ease of illustration this second charging module is not shown.

Transceiver unit 209, receiver unit 208, power transmitter unit 313, and data transmitter unit 321 are configured to establish a transcutaneous communication link in which data and power is inductively transmitted to receiver unit 208. The transcutaneous communication link, represented by arrows 570, 572 and 578 uses time interleaving of power and data on a single frequency channel to transmit the power and data to receiver unit 208. As noted, the time interleaving uses successive time frames, each having a time length and each divided into two or more time slots. Within each frame, one or more time slots are allocated to power transmitter unit 313 and one or more time slots are allocated to data transmitter unit 321. Data transmitter unit 321 and power transmitter unit are configured to transmit data and power, respectively, within their allocated time slots.

In one embodiment of FIG. 5E, the time interleaving scheme comprises successive frames each divided into two time slots. Within each frame, one time slot is allocated to data transmitter unit 321. During this first time slot of each frame, data 570 is inductively transmitted by unit 321 to receiver unit 208 and to transceiver unit 209. In these embodiments, data 578 and data 570 are the same data. A second time slot within the successive frames is allocated to power transmitter 313. During this second time slot of each frame, power 572 is inductively transmitted by unit 313 to receiver unit 208.

In certain embodiments of the present invention, data 570 transmitted by data transmitter unit 321 may also be received by a data receiver 314 (shown in FIG. 3A) within power transmitter 313. In these embodiments, transmitted data 570 is used by power transmitter unit 313 to synchronize the transmission of power 572 within allocated time slots. For example, in embodiments of the present invention, data module 214 includes the system clock which provides a common time base for the transfer of data and power within the transcutaneous communication link. Transmitted data 570 may include a timing reference that enables power transmitter unit 313 to remain synchronized with the system clock. This synchronization prevents collisions between transmitted data 570 and power 572.

The first and second time slots may be allocated to power transmitter unit 313 and data transmitter unit 321 as described above with reference to FIGS. 4A-4E. For example, as described above, the first and second time slots may be allocated in a predetermined manner prior to transmitting, dynamically in real time, etc.

In an alternative embodiment of FIG. 5E, the time interleaving scheme comprises successive frames each divided into three time slots. Within each frame, two time slots are allocated to data transmitter unit 321. During one of these time slots of each frame, data 570 is inductively transmitted by unit 321 to receiver unit 208. In the second time slot allocated to data transmitter unit 321, data 578 is transmitted to transceiver unit 209. In these embodiments, data 578 and data 570 are different data. The third time slot within the successive frames is allocated to power transmitter 313. During this second time slot of each frame, power 572 is inductively transmitted by unit 313 to receiver unit 208. As explained above, the transmitted data may be used to synchronize the transmission of power 572 within allocated time slots.

The first, second and third time slots may be allocated to power transmitter unit 313 and data transmitter unit 321 as described above with reference to FIGS. 4A-4E. For example, as described above, the first and second time slots may be allocated in a predetermined manner prior to transmitting, dynamically in real time, etc.

Figure 6:
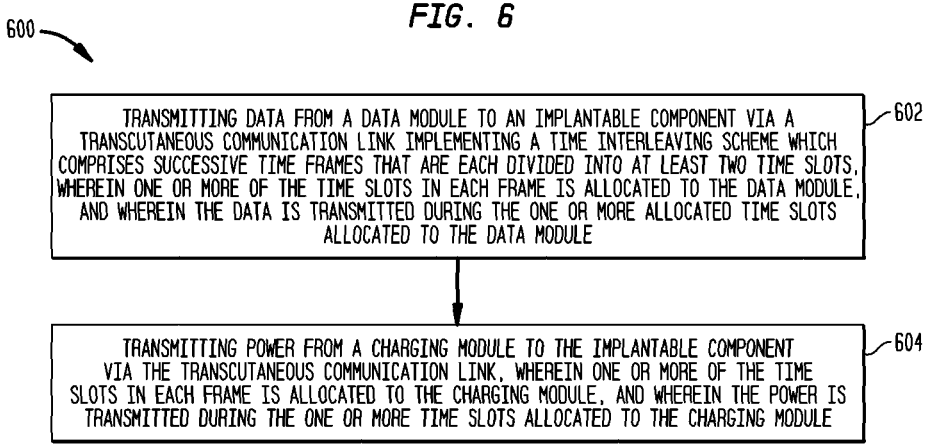
FIG. 6 is a flowchart illustrating the operations performed by an implantable medical device in accordance with embodiments of the present invention.

FIG. 6A is a flowchart illustrating the operations performed to provide wireless communication in a medical device in accordance with embodiments of the present invention. The medical device configured to implement method 600 of FIG. 6A comprises an implantable component having a receiver unit, an external charging module having a power transmitter unit and a data module having a data transmitter unit. At block 602, data is transmitted from the data transmitter unit to the receiver unit in the implantable component. The data is transmitted via a transcutaneous communication link implementing a time interleaving scheme. As described above, the time interleaving scheme comprises successive time frames each divided into at least two time slots. One or more of the time slots in each frame is allocated to the data transmitter unit, and the data is transmitted by the unit during the one or more allocated time slots. At block 604, power is transmitted from the charging module to the implantable component via the transcutaneous communication link. One or more of the time slots in each frame is allocated to the data transmitter unit, and the data is transmitted during the one or more allocated time slots.

In practical systems, it is important to be aware that during unused timeslots of the external charging module (when no power is transmitted), the external coil within the power transmitter unit should be disconnected from its generator and connected to a data receiver with very high input impedance. This is useful to minimize influence on the performance of the implantable coil.

Furthermore, it would be appreciated that the above described an implantable coil would include a resonance circuit to optimize performance. Depending on the type of magnetic induction link utilized (i.e. weakly coupled or closely coupled magnetic link), the implantable coil needs to be tuned slightly different. This may be achieved, for example, by adding or removing capacitance from the resonance circuit.

Furthermore, while the previous examples describe magnetic inductive power transfer, the power transfer of the external charging device is not limited to magnetic induction using two closely coupled coils. One possible alternative power transfer mechanism is to use the charge displacement currents between conductive surfaces (plates) of the external and implanted devices that are capacitive coupled to each other, referred to as capacitive coupling. Another type of power transfer is based on electromagnetic waves. It would also be appreciated that the mechanism used to transfer data is also not limited to magnetic induction and may include, for example, capacitive data links.

As one of ordinary skill in the art would appreciate, implantable medical devices envisaged by the present invention include, but are not limited to, cochlear implants, nerve stimulators, pace makers, glucose meters, and any other type of implantable medical device requiring wireless communication.

For example, embodiments of the present invention may be implemented in an active medical device. An active medical is any medical device relying for its functioning on a source of electrical energy or any source of power other than that directly generated by the human body or by gravity. An active implantable medical device (AIMD) is any active medical device which is intended to be totally or partially introduced, surgically or medically, into the human body or by medical intervention into a natural orifice, and which is intended to temporarily or permanently remain in the patient after the procedure.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A cochlear implant comprising:
an implantable component having an electrode assembly insertable in a recipient's cochlea and a stimulator/receiver unit configured to deliver stimulation signals to the recipient's cochlea via the electrode assembly;
an external charging module having a power transmitter unit; and
a data module that is physically separate from the external charging module, wherein the data module comprises a data transmitter unit;
wherein the data transmitter unit and the power transmitter unit are each configured to establish a transcutaneous communication link with the implantable component over which data and power, respectively, are transmitted on a single shared frequency channel, and wherein the data transmitter unit and the power transmitter unit collectively implement a time interleaving scheme comprising successive frames each divided into at least two time slots in order to share the single shared frequency channel;
wherein one or more of the time slots in each frame is allocated to the data transmitter unit and one or more of the time slots in each frame is allocated to the power transmitter unit,
wherein data and power are transmitted by the transmitter units during different time slots;
wherein the one or more time slots in each frame are dynamically allocated to the power transmitter unit and the data transmitter unit in real-time based on a state of the cochlear implant; and
wherein the data module and external charging module are configured to directly exchange data with one another to synchronize the transmission of power and data on the single shared frequency channel.

2. The cochlear implant of claim 1, wherein the power transmitter unit and the data transmitter unit each comprise a magnetic induction coil, and wherein the transcutaneous communication link comprises a magnetic induction link.

3. The cochlear implant of claim 1, wherein after one or more time slots in a frame are dynamically allocated to the power transmitter unit, the power transmitter unit is configured to verify that the one or more time slots dynamically allocated thereto are unoccupied prior to transmitting power within the one or more time slots.

4. The cochlear implant of claim 1, wherein the power transmitter unit includes a data receiver configured to receive data transmitted by the data transmitter unit, and wherein the received data is used by the power transmitter unit to synchronize transmission of power into the one or more time slots allocated to the power transmitter unit.

5. The cochlear implant of claim 1, wherein the data module is an external device.

6. The cochlear implant of claim 5, wherein the data module comprises:
a microphone to receive a sound and to convert the sound into electrical signals, and wherein the data transmitter unit is configured to transmit the electrical signals output by the microphone to the implantable component in the one or more time slots allocated thereto.

7. The cochlear implant of claim 5, wherein the data module comprises:
a microphone to receive a sound and to convert the sound into electrical signals; and
a sound processor configured to convert the electrical signals into encoded data signals, wherein the data transmitter unit is configured to transmit the encoded data signals to the implantable component in the one or more time slots allocated thereto.

8. The cochlear implant of claim 1, wherein the implantable component further comprises a transceiver unit configured to transmit data, the transceiver unit forming a component of the transcutaneous communication link, and wherein one or more of the time slots in each frame are allocated to the transceiver unit, and wherein data is transmitted by the transceiver unit during the time slots allotted thereto.

9. The cochlear implant of claim 1, wherein the external charging module comprises:
a housing having a power source, the power transmitter unit therein;
a coil attached to the exterior of the housing; and
a magnet configured to attach the charging module to the recipient via magnetic coupling with a magnet in the implantable component.

10. The cochlear implant of claim 9, wherein the charging module comprises:
a housing having a power source and the power transmitter unit therein;
a coil connected to the power transmitter unit via a cable, the coil having a magnet attached thereto to couple the coil to the recipient via magnetic coupling with a magnet in the implantable device.

11. The cochlear implant of claim 1, further comprising:
a second implantable component, wherein the second implantable component comprises a transceiver unit configured to transmit data, the transceiver unit forming a component of the transcutaneous communication link.

12. The cochlear implant of claim 11, wherein one or more of the time slots in each frame are allocated to the transceiver unit, and wherein data is transmitted by the transceiver unit during the time slots allotted thereto.

13. The cochlear implant of claim 1, wherein two or more successive time slots are allocated to data or two or more successive time slots are allocated to power.

14. A method of wireless communication in a medical device comprising an implantable component having a receiver unit, an external charging module having a power transmitter unit, and a data module having a data transmitter unit, wherein the data module is physically separate from the external charging module, the method comprising:
transmitting data from the data transmitter unit to the receiver unit on a single shared frequency channel via a transcutaneous communication link used as part of a time interleaving scheme comprising successive time frames each divided into at least two time slots, wherein one or more of the time slots in each frame are allocated to the data transmitter unit, and wherein the data is transmitted during the one or more time slots allocated thereto; and
transmitting power from the power transmitter unit to the receiver unit on the shared frequency channel via a transcutaneous communication link used as part of the time interleaving scheme, wherein one or more of the time slots in each frame are allocated to the data the power transmitter unit, wherein the power is transmitted during the one or more time slots allocated thereto;
dynamically allocating the one or more time slots in each frame to the power transmitter unit and the data transmitter unit in real-time based on a state of the medical device; and
synchronizing the transmission of power and data on the single shared frequency channel by wirelessly exchanging data between the data module and the external charging module.

15. The method of claim 14, further comprising:
transmitting the power and data via magnetic induction link.

16. The method of claim 14, wherein the power transmitter unit comprises a data receiver to receive data transmitted by the data transmitter unit, and wherein synchronizing the transmission of power and data on the shared frequency channel by wirelessly exchanging data between the data module and the external charging module comprises:
synchronizing the transmission of power into the one or more time slots allocated to the power transmitter unit based on the data received by the data receiver.

17. The method of claim 14, after one or more time slots in a frame are dynamically allocated to the power transmitter unit, the method further comprises:
verifying by the power transmitter unit that the one or more time slots dynamically allocated thereto are unoccupied prior to transmitting power within the one or more time slots.

18. The method of claim 14, wherein two or more successive time slots are allocated to data or two or more successive time slots are allocated to power.

19. A medical device comprising:
an implantable component having a receiver unit;
an external charging module having a power transmitter unit; and
a data module that is physically separate from the external charging module, wherein the data module comprises data transmitter unit;
wherein the data transmitter unit and the power transmitter unit are each configured to establish a transcutaneous communication link over which data and power, respectively, are transmitted on a single shared frequency channel, and wherein the data transmitter unit and the power transmitter unit collectively implement a time interleaving scheme comprising successive frames each divided into at least two time slots in order to share the single shared frequency channel;
wherein one or more of the time slots in each frame are dynamically allocated to the data transmitter unit and one or more of the time slots in each frame are dynamically allocated to the power transmitter unit;

wherein data and power are transmitted by the transmitter units during different time slots, wherein the one or more time slots in each frame are dynamically allocated to the power transmitter unit and the data transmitter unit in real-time based on a state of the medical device, and wherein the data module and external charging module are configured to directly exchange data with one another to synchronize the transmission of power and data on the single shared frequency channel.

20. The medical device of claim 19, wherein the power transmitter unit and the data transmitter unit each comprise a magnetic induction coil, and wherein the transcutaneous communication link comprises a magnetic induction link.

21. The medical device of claim 19, wherein after one or more time slots in a frame are dynamically allocated to the power transmitter unit, the power transmitter unit is configured to verify that the one or more time slots dynamically allocated thereto are unoccupied prior to transmitting power within the one or more time slots.

22. The medical device of claim 19, wherein the power transmitter unit includes a data receiver configured to receive data transmitted by the data transmitter unit, and wherein the received data is used by the power transmitter unit to synchronize transmission of power into the one or more time slots allocated to the power transmitter unit.

23. The medical device of claim 19, wherein the data module is an external device.

24. The medical device of claim 23, wherein the data module comprises:
a microphone to receive a sound and to convert the sound into electrical signals, and wherein the data transmitter unit is configured to transmit the electrical signals output by the microphone to the implantable component in the one or more time slots allocated thereto.

25. The medical device of claim 23, wherein the data module comprises:
a microphone to receive a sound and to convert the sound into electrical signals; and
a sound processor configured to convert the electrical signals into encoded data signals, wherein the data transmitter unit is configured to transmit the encoded data signals to the implantable component in the one or more time slots allocated thereto.

26. The medical device of claim 19, wherein the implantable component further comprises a transceiver unit configured to transmit data, the transceiver unit forming a component of the transcutaneous communication link, and wherein one or more of the time slots in each frame are allocated to the transceiver unit, and wherein data is transmitted by the transceiver unit during the time slots allotted thereto.

27. The medical device of claim 19, wherein the external charging module comprises:
a housing having a power source, the power transmitter unit therein;
a coil attached to the exterior of the housing; and
a magnet configured to attach the charging module to the recipient via magnetic coupling with a magnet in the implantable component.

28. The medical device of claim 27, wherein the charging module comprises:
a housing having a power source and the power transmitter unit therein;
a coil connected to the power transmitter unit via a cable, the coil having a magnet attached thereto to couple the coil to the recipient via magnetic coupling with a magnet in the implantable device.

29. The medical device of claim 19, further comprising:
a second implantable component, wherein the second implantable component comprises a transceiver unit configured to transmit data, the transceiver unit forming a component of the transcutaneous communication link.

30. The medical device of claim 29, wherein one or more of the time slots in each frame are allocated to the transceiver unit, and wherein data is transmitted by the transceiver unit during the time slots allotted thereto.

31. The medical device of claim 19, wherein two or more successive time slots are allocated to data or two or more successive time slots are allocated to power.

* * * * *